US00PP10477P

United States Patent [19]

Meilland

[11] Patent Number: Plant 10,477

[45] Date of Patent: Jul. 7, 1998

[54] ROSE PLANT NAMED 'MEIPARNIN'

[75] Inventor: Alain A. Meilland, Antibes, France

[73] Assignee: The Conard-Pyle Company, West Grove, Pa.

[21] Appl. No.: 834,864

[22] Filed: Apr. 10, 1997

[51] Int. Cl.[6] ..... A01H 5/00

[52] U.S. Cl. ..... Plt./11

[58] Field of Search ..... Plt./11, 15, 18

*Primary Examiner*—Howard J. Locker

*Attorney, Agent, or Firm*—Burns, Doane, Swecker & Mathis, L.L.P.

[57] ABSTRACT

A new and distinct variety of Hybrid Tea rose plant is provided which abundantly forms attractive very large blossoms that are Cream Yellow and bordered and suffused with light Carmine Rose. Such blossoms additionally exhibit a subtle peach-like fragrance. The plant exhibits medium green and bright foliage, as well as good disease resistance. The new variety is particularly well suited for growing as attractive ornamentation in the landscape or for use when forming cut flowers.

1 Drawing Sheet

SUMMARY OF THE INVENTION

The new variety of Hybrid Tea rose plant was created by artificial pollination wherein two parents were crossed which previously had been studied in the hope that they would contribute the desired characteristics. The female parent (i.e., the seed parent) of the new variety was the product of the cross of the 'Meicapula' variety (non-patented in the United States) and the 'Korav' variety (non-patented in the United States). The male parent (i.e., the pollen parent) was the 'Delboip' variety (non-patented in the United States). The parentage of the new variety can be summarized as follows:

('Meicapula'×'Korav')×'Delboip'.

The seeds resulting from the above pollination were sown and small plants were obtained which were physically and biologically different from each other. Selective study resulted in the identification of a single plant of the new variety.

It was found that the new variety of Hybrid Tea rose plant of the present invention possesses the following combination of characteristics:

(a) forms in abundance attractive very large Cream Yellow blossoms that are bordered and suffused with light Carmine Rose and possess a subtle peach-like fragrance,
(b) exhibits a semi-erect growth habit,
(c) forms attractive medium green and glossy foliage, and
(d) exhibits good disease resistance.

The new variety well meets the needs of the horticultural industry and is particularly well adapted for use as an attractive ornamental plant in an outdoors environment or for cut flower production.

The new variety has been found to undergo asexual propagation in France by a number of routes, including budding, grafting, and cuttage. Asexual propagation by the above-mentioned techniques in France has shown that the characteristics of the new variety are stable and are strictly transmissible by such asexual propagation from one generation to another.

The new variety has been named the 'Meiparnin' variety.

BRIEF DESCRIPTION OF THE PHOTOGRAPH

The accompanying photograph shows as nearly true as it is reasonably possible to make the same, in a color illustration of this character, typical specimens of the plant parts of the new variety. The rose plants of the new variety were two years of age and were observed during June while budded on *Rosa froebelii* understock and growing outdoors at Le Cannet des Maures, Var, France. Dimensions in centimeters are indicated at the bottom of the photograph.

Detailed Description

Figures 1, 2, 3, 4, 5, 6, 7, 8, 9, 10, 11, 12, 13, 14, 15, 16:
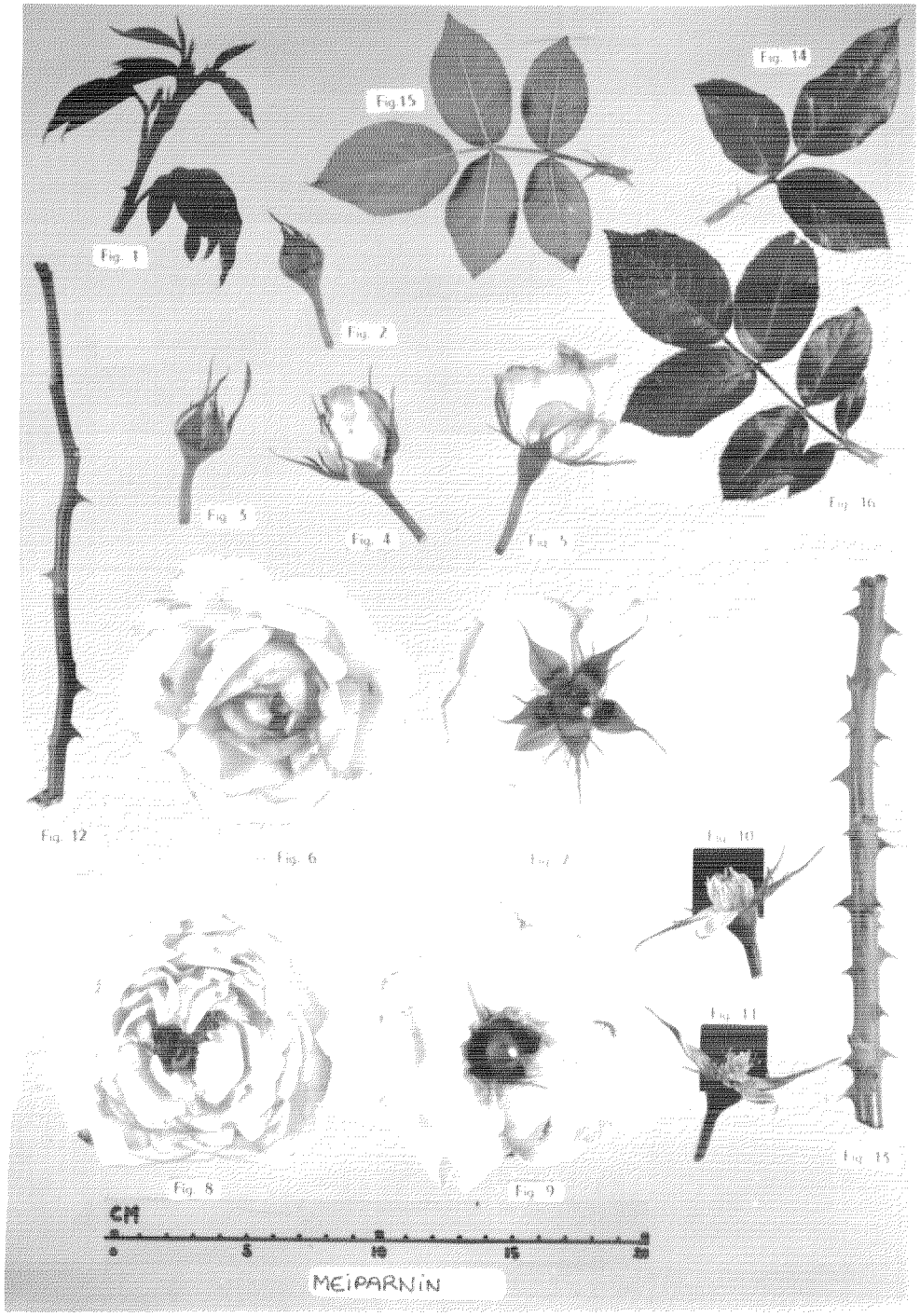
FIG. 1 illustrates a specimen of a young shoot.
FIG. 2 illustrates a specimen of a floral bud before the opening of the sepals.
FIG. 3 illustrates a specimen of a floral bud at the opening of the sepals.
FIG. 4 illustrates a specimen of a floral bud at the opening of the petals.
FIG. 5 illustrates a specimen of a flower in the course of opening.
FIG. 6 illustrates a specimen of an open flower—plan view—obverse.
FIG. 7 illustrates a specimen of an open flower—plan view—reverse.
FIG. 8 illustrates a specimen of a fully open flower—plan view—obverse.
FIG. 9 illustrates a specimen of a fully open flower—plan view—reverse.
FIG. 10 illustrates a specimen of a floral receptacle showing the arrangement of the stamens and pistils.
FIG. 11 illustrates a specimen of a floral receptacle showing the arrangement of the pistils (stamens removed)
FIG. 12 illustrates a specimen of a flowering stem.
FIG. 13 illustrates a specimen of a main branch.
FIG. 14 illustrates a specimen of a leaf with three leaflets—plan view—upper surface.
FIG. 15 illustrates a specimen of a leaf with five leaflets—plan view—under surface.
FIG. 16 illustrates a specimen of a leaf with seven leaflets—plan view—upper surface.

The chart used in the identification of the colors is that of The Royal Horticultural Society (R.H.S. Colour Chart). The description is based on the observation of two year-old plants during June while budded on *Rosa froebelii* understock and growing outdoors at Le Cannet des Maures, Var, France. The coloration in common terms precedes reference to the chart in some instances.

Class: Hybrid Tea.

Plant:

*Height.*—Approximately 90 to 110 cm. on average.

*Habit.*—Semi-erect.

Branches:

*Color.*—young stems: light green, yellow-green group 146C. Adult wood: medium green, Green group 143C.

*Thorns.*—Size: medium. Quantity: numerous. Color: pinkish-green on young stems and reddish on adult wood.

Leaves:

*Stipules.*—Adnate, pectinate, linear and moderately large.

*Petioles.*—Upper surface: grooved with reddish brown on young foliage, and medium green on adult foliage with glandular sides. Under surface: light green with some small thorns.

*Leaflets.*—Number: 3, 5 (most often), and 7. Shape: elliptic. Serration: simple and regular (as illustrated). Texture: leathery. General appearance: dense and bright. Color (young foliage): Upper surface: medium green, yellow-green group 146B, and more or less stained with reddish brown. Under surface: reddish brown. Color (adult foliage): Upper surface: bronze green, Yellow-green group 146A. Under surface: light green, green group 137C.

*Inflorescence:*

*Number of flowers.*—Usually one to three per stem.

*Peduncle.*—Light green, more or less toned with reddish coloration, glandular, and the length is approximately 13.5 cm. on average.

*Sepals.*—Upper surface: tomentose, and greenish in coloration. Under surface: medium green and more or less toned with reddish coloration, very glandular external sepals, and commonly possess a few extensions.

*Bud.*—Shape: globular. Length: approximately 3.5 cm. on average. Size: large. Color upon opening: Upper surface: light Cream Yellow., Yellow group 4D, bordered and lightly suffused with light Carmine Rose. Red Group 52C, and commonly possess a base of Sap Green. Under surface: Sap Green, yellow-green Group 150D.

*Flower.*—Shape: old rose with the configuration of a hollow cup with a rounded heart. Diameter: approximately 13.5 cm. on average. Color (when opening begins): Upper surface: near light Cream Yellow, yellow group 4D, and bordered and lightly suffused with light Carmine Rose, red group 52C. Under surface: near light Cream Yellow, yellow group 4D, and bordered and lightly suffused with light Carmine Rose, red group 52C. Color (when blooming): Upper surface: near light Cream Yellow, yellow group 4D, and bordered and lightly suffused with light Carmine Rose, red (group 52C. Under surface: near light Cream Yellow, yellow group 4D, and bordered and lightly suffused with light Carmine Rose, red group 52C. Color (at end of opening): Upper surface: near light Cream Yellow, yellow group 4D, and bordered and lightly suffused with light Carmine Rose, Red Group 52C. Under surface: near light Cream Yellow, Yellow Group 4D, and bordered and lightly suffused with light Carmine Rose, Red Group 52C. Fragrance: subtle peach-like perfume. Petal number: approximately 58 on average. Petal shape: the base is rounded to flattened (as illustrated). Stamen number: approximately 580 on average. Anthers: light ochre and sometimes toned with reddish coloration. Filaments: straw colored and very tomentose on the base. Pistil number: approximately 380 on average. Stilmas: ochre and light fuchsia in coloration. The filaments and styles sometimes are intermixed in a very tomentose receptacle. Styles: often present with a vegetative Receptacle: medium green, and in longitudinal section in the shape of a broad funnel.

Development:

*Vegetation.*—Very strong.

*Blooming.*—Very abundant and recurrent.

*Resistance to diseases.*—Very good.

1. A new and distinct variety of Hybrid Tea rose plant characterized by the following combination of characteristics:

(a) forms in abundance attractive very large Cream Yellow blossoms that are bordered and suffused with light Carmine Rose and possess a subtle peach-like fragrance, (b) exhibits a semi-erect growth habit, (c) forms attractive medium green and glossy foliage, and (d) exhibits good disease resistance:

substantially as herein shown and described.

* * * * *

CM
0
5
10
15
20
MEIPARNIN